(12) United States Patent
Kolel-Veetil et al.

(10) Patent No.: US 8,217,194 B2
(45) Date of Patent: Jul. 10, 2012

(54) POLYARYLACETYLENES CONTAINING SILOXANE, SILANE, AND CARBORANE MOIETIES

(75) Inventors: Manoj K. Kolel-Veetil, Alexandria, VA (US); Teddy M Keller, Fairfax Station, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 13/157,573

(22) Filed: Jun. 10, 2011

(65) Prior Publication Data

US 2011/0306744 A1 Dec. 15, 2011

Related U.S. Application Data

(60) Provisional application No. 61/353,690, filed on Jun. 11, 2010.

(51) Int. Cl.
*C04B 35/524* (2006.01)
*C08G 77/00* (2006.01)
*C08G 79/08* (2006.01)
*C07F 7/02* (2006.01)
*C07F 7/08* (2006.01)

(52) U.S. Cl. .................................. 556/403; 526/239

(58) Field of Classification Search .................. None
See application file for complete search history.

(56) References Cited

U.S. PATENT DOCUMENTS

| | | | |
|---|---|---|---|
| 4,208,492 A | 6/1980 | Hedaya et al. | |
| 5,272,237 A | 12/1993 | Keller et al. | |
| 5,292,779 A | 3/1994 | Keller et al. | |
| 5,348,917 A | 9/1994 | Keller et al. | |
| 5,483,017 A | 1/1996 | Keller et al. | |
| 5,552,505 A | 9/1996 | Keller | |
| 5,679,818 A | 10/1997 | Bucca et al. | |
| 5,756,629 A | 5/1998 | Keller et al. | |
| 5,780,569 A | 7/1998 | Keller et al. | |
| 5,807,953 A | 9/1998 | Bucca et al. | |
| 5,932,335 A | 8/1999 | Keller et al. | |
| 5,969,072 A | 10/1999 | Keller et al. | |
| 5,981,678 A | 11/1999 | Keller et al. | |
| 6,187,703 B1 | 2/2001 | Keller et al. | |
| 6,187,890 B1 | 2/2001 | Fehn et al. | |
| 6,225,247 B1 | 5/2001 | Keller et al. | |
| 6,265,336 B1 | 7/2001 | Keller et al. | |
| 6,967,233 B2 | 11/2005 | Keller | |
| 7,153,921 B2 | 12/2006 | Keller et al. | |
| 7,238,766 B2 | 7/2007 | Keller et al. | |
| 7,411,030 B2 | 8/2008 | Keller | |
| 7,449,535 B2 | 11/2008 | Keller et al. | |
| 7,576,168 B2 | 8/2009 | Keller et al. | |
| 7,579,424 B2 | 8/2009 | Keller et al. | |
| 7,579,430 B2 | 8/2009 | Keller et al. | |
| 7,605,218 B2 | 10/2009 | Keller et al. | |
| 7,649,070 B2 | 1/2010 | Keller | |
| 7,655,738 B2 | 2/2010 | Keller et al. | |
| 7,897,715 B1 | 3/2011 | Laskoski et al. | |
| 7,923,523 B2 | 4/2011 | Keller et al. | |
| 2004/0024163 A1 | 2/2004 | Levassort et al. | |
| 2009/0239070 A1 | 9/2009 | Keller et al. | |
| 2010/0267913 A1 | 10/2010 | Kolel-Veetil et al. | |

FOREIGN PATENT DOCUMENTS

| | | |
|---|---|---|
| CN | 1709928 A | 12/2005 |
| JP | 3602701 | 4/2009 |

OTHER PUBLICATIONS

Sugimoto et al. Organosilicon chemistry IV, 2000, 620-625.*
Search Report and Written Opinion in PCT/US11/39925 (Oct. 24, 2011).
Gao et al., "Synthesis and Properties of Arylacetylene Resins with Siloxane Units" Bull. Korean Chem. Soc. 2010, vol. 31, No. 4, 976-980 (Apr. 20, 2010).
Henderson et al., "Synthesis and Characterization of Poly (carborane-siloxane-acetylene)" Macromolecules 1994,27, 1660-1661.
Ichitani et al., "Silyl-Carborane Hybridized Diethynylbenzene-Silylene Polymers" Polymer Journal, 31(11-1), 908-912 (1999).
Kimura et al., "Structural Study of Silyl-Carborane Hybrid Diethynylbenzene-Silylene Polymers by High-Resolution Solid-State 11B, 13C, and 29Si NMR Spectroscopy" Chem. Mater. 2003, 15, 355-362.
Sergeyev et al., "Carborane-containing poly(arylacetylenes)" Polymer Science U.S.S.R., 28(11), 2638-2641 (1986) (abstract only).
Son et al., "Synthesis and Characterization of Linear Siloxane-Diacetylene Polymers" Macromolecules 1996,28, 399-400.
Wang et al.,"Synthesis and characterization of thermooxidatively stable poly (dimethylsilyleneethynylenephenyleneethynylene) with o-carborane units" Reactive & Functional Polymers (May 18, 2011).

* cited by examiner

*Primary Examiner* — Yevegeny Valenrod
(74) *Attorney, Agent, or Firm* — Amy L Ressing; Joseph Trent Grunkemeyer (57) ABSTRACT

Disclosed herein are the compounds shown below. Each R is an organic group, Cb is a carborane group, and —$C_6H_4$— is phenylene. The value of each m is a nonnegative integer, q is 0 or 1, with the proviso that if q is 0 then m is 0 or 1, p is a positive integer, r is a positive integer, and n is an integer greater than or equal to 10. Also disclosed are methods of making and crosslinking the compounds.

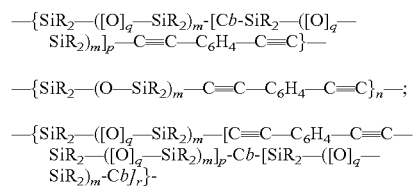

16 Claims, 7 Drawing Sheets

POLYARYLACETYLENES CONTAINING SILOXANE, SILANE, AND CARBORANE MOIETIES

This application claims the benefit of U.S. Provisional Application No. 61/353,690, filed on Jun. 11, 2010. The provisional application and all other publications and patent documents referred to throughout this nonprovisional application are incorporated herein by reference.

TECHNICAL FIELD

The present disclosure is generally related to polyarylacetylenes containing siloxane or silane and carborane moieties.

DESCRIPTION OF RELATED ART

Carboranylenesiloxanes are highly sought after high temperature, thermally and thermo-oxidatively stable materials, which have been of particular interest to aerospace and defense industries (Dvornic, P. R., Lenz, R. W. *High temperature Siloxane Elastomers*; Huthig & Wepf: Heidelberg, Germany 1990). These materials are unmatched, especially, when it comes to their thermo-oxidative stabilities at very high temperatures. However, linear carboranylenesiloxane polymers that are low molecular weight oligomers preclude their use in applications requiring high molecular weight materials ((i) Papetti et al., *J. Polym. Sci.* Part A-1, 4, 1966, 1623. (ii) Mayes et al., *J. Polym. Sci.* Part A-1, 5, 1967, 365). A solution to this problem was the introduction of unsaturated cross-linkable units in such materials, which on curing yielded extended polymer networks of sufficient strength for various applications (Henderson et al., *Macromolecules* 1994, 27, 1660). This class of polymers, commonly known as PCSA polymers that is currently being produced in industry, has already started finding application as coating insulations for cables and as thermo-oxidatively stable adhesives.

BRIEF SUMMARY

Disclosed herein is a compound comprising the repeat unit:

—{SiR$_2$—([O]$_q$—SiR$_2$)$_m$-[C$b$-SiR$_2$—([O]$_q$—SiR$_2$)$_m$]$_p$—C≡C—C$_6$H$_4$—C≡C}—.

Each R is an independently selected organic group, Cb is a carborane group, and —C$_6$H$_4$— is phenylene. The value of each m is a nonnegative integer, q is 0 or 1, with the proviso that if q is 0 then m is 0 or 1, and p is a positive integer.

Also disclosed herein is a method comprising: providing an acetylene-containing compound having the formula:

M-C≡C—C$_6$H$_4$—C≡C-M, and reacting the acetylene-containing compound with a carborane-containing compound having the formula:

X—SiR$_2$—([O]$_q$—SiR$_2$)$_m$-[C$b$-SiR$_2$—([O]$_q$—SiR$_2$)$_m$]$_p$—X.

M is Li, Na, K, or MgX', wherein X' is a halogen. The product of the reaction is the above compound.

Also disclosed herein is a method comprising: providing an acetylene-siloxane-carborane compound having the formula:

HC≡C—SiR$_2$—([O]$_q$—SiR$_2$)$_m$-[C$b$-SiR$_2$—([O]$_q$—SiR$_2$)$_m$]$_p$—C≡CH, and reacting the acetylene-siloxane-carborane compound with a phenyl-containing compound having the formula under metal-catalyzed coupling conditions:

X—C$_6$H$_4$—X.

The product of the reaction is the above compound.

Also disclosed herein is a polymer comprising the formula:

—{SiR$_2$—(O—SiR$_2$)$_m$—C≡C—C$_6$H$_4$—C≡C}$_n$—.

The value of n is an integer greater than or equal to 10.

Also disclosed herein is a method comprising: providing the above acetylene-containing compound, and reacting the acetylene-containing compound with a siloxane-containing compound having the formula:

X—SiR$_2$—(O—SiR$_2$)$_m$—X.

The product of the reaction is the above polymer.

Also disclosed herein is a compound comprising the repeat unit:

—{SiR$_2$—([O]$_q$—SiR$_2$)$_m$—[C≡C—C$_6$H$_4$—C≡C—SiR$_2$—([O]$_q$—SiR$_2$)$_m$]$_p$-C$b$-[SiR$_2$—([O]$_q$—SiR$_2$)$_m$-C$b$]$_r$}-.

The value of r is a positive integer.

Also disclosed herein is a method comprising: providing an acetylene-containing compound having the formula:

M-C≡C—C$_6$H$_4$—C≡C-M, and reacting the acetylene-containing compound with an excess of a silane or siloxane compound having the formula:

X—SiR$_2$—([O]$_q$—SiR$_2$)$_m$—X, to form a first intermediate having the formula:

X—SiR$_2$—([O]$_q$—SiR$_2$)$_m$—[C≡C—C$_6$H$_4$—C≡C—SiR$_2$—([O]$_q$—SiR$_2$)$_m$]$_p$—X, separately reacting the silane or siloxane compound with an excess of a carborane compound having the formula:

M'-C$b$-M', wherein M' is Li, Na, K, or MgX' and the product of the separate reaction is a second intermediate having the formula:

M'-C$b$-[SiR$_2$—([O]$_q$—SiR$_2$)$_m$-C$b$]$_r$-M', and reacting the first intermediate with the second intermediate to form the above compound.

BRIEF DESCRIPTION OF THE DRAWINGS

A more complete appreciation will be readily obtained by reference to the following Description of the Example Embodiments and the accompanying drawings.

DETAILED DESCRIPTION OF EXAMPLE EMBODIMENTS

In the following description, for purposes of explanation and not limitation, specific details are set forth in order to provide a thorough understanding of the present disclosure. However, it will be apparent to one skilled in the art that the present subject matter may be practiced in other embodiments that depart from these specific details. In other instances, detailed descriptions of well-known methods and devices are omitted so as to not obscure the present disclosure with unnecessary detail.

Disclosed herein is the synthesis of novel inorganic-organic hybrid polymers containing siloxane or silane, carborane, and phenylacetylene groups and their conversion into networked or crosslinked polymers that are known to possess exceptional thermal, thermo-oxidative, electrical, adhesive (coating/surface) and membrane properties. As used herein, the term "polymer" includes linear polymers and oligomers with no upper or lower limit on molecular weight unless stated. A "compound" that comprises a repeat unit includes such polymers and oligomers, or may include only one copy of the repeat unit. Above, 500° C., the crosslinked polymers are converted into ceramics that are thermally and oxidatively stable to at least 1500° C. In contrast to the previous systems that contain only siloxane, silane, carborane, and acetylene units through which the conversion to the crosslinked system occurs, the inclusion of the aromatic units (aryl) can enhance the mechanical properties of the plastics or elastomers, which is very beneficial for structural and coating applications. The great demand for such high performance materials stems from their use in a wide variety of engineering applications that require unusual service conditions. The materials are needed especially for applications in aerospace and defense industries such as sealing assemblies for engine components, landing gears, flight control and fuel systems, and in coating insulations for cables.

Previous research with poly(carborane-siloxane-acetylene)s (PCSAs) had demonstrated that there was a marked dependence on the thermal and material properties of the PCSAs on the copolymer sequence, i.e. in the way the siloxane, carborane, and acetylene components are present in the produced polymer chains (Kolel-Veetil et al., *Chem. Mater.* 2004, 16, 3162-3167). Both alternating and copolymer variants of PCSAs were found to have pronounced differences in their material properties. In light of this, the development of similar polyarylacetylenes was pursued. Both alternating and copolymer variants require the reaction to be performed in two flasks, the products of which are subsequently reacted to produce the chain-extended final products.

The structure of the disiloxane version of the PCSAs with a carborane:siloxane:diacetylene ratio of 1:2:1 is shown below. The processability of the PCSAs may be further improved by the introduction of aromatic components in their backbone, which should enhance the toughness of the corresponding crosslinked or thermosetting polymers. To this avail, a beneficial group that is worth the incorporation is the diethynylbenzene group, which is a variant of the diacetylene group of the PCSA polymers by virtue of the presence of a phenyl group in between the two acetylene groups of the diacetylene group.

PCSA Polymer

There are three variants of diethynylbenzene group, namely, 1,2-diethynylbenzene, 1,3-diethynylbenzene and 1,4-diethynylbenzene all of which are intended for utilization herein. The relative positions of the two ethynyl groups on the aromatic ring can dictate the steric natures of the linear polymers that they produce and the rates of the polymerization reactions. They can also subsequently dictate the nature and efficacy of the crosslinking/curing process that the resultant polymers undergo. Although some of the examples herein involve 1,3-diethynylbenzene, and the others involve 1,4-diethynylbenzene, all such examples are equally feasible with either of them and also by 1,2-diethynylbenzene. Hence, the three diethynylbenzenes can be interchangeably used in the disclosed examples. It is expected that in some cases 1,4-diethynylbenzene may be more suitable from a steric point of view more so than 1,2-diethynylbenzene, and also than 1,3-diethynylbenzene, as the linear polymeric products formed from it may have less steric crowding around the ethynyl and phenyl moieties that are intended as sites of crosslink-formation. Furthermore, the packing of the 1,4-diethynylbenzene moieties prior to crosslinking may be more efficient than with 1,3-diethynylbenzene or 1,2-diethynylbenzene moieties which may lead to an enhanced degree of crosslinking and thus, would perhaps result in crosslinked networks with altered mechanical (material) properties.

The introduction of the aromatic group may increase chain stiffness and consequently improve the mechanical properties of the polymer. The presence of the aromatic groups in the chain can also improve the stability of the polymers against chemical agents and further improve thermal stability. For example, aromatic groups are known to exhibit resistance to free-radical attack and degradation (Pospisil, *Advances in Polymer Science* 1995, 124, 89-189).

It is also known that the incorporation of an aromatic unit into the backbone of poly(dimethylsiloxane) improves both its mechanical and thermal properties and reduces depolymerization to small cyclic compounds at elevated temperatures relative to poly(dimethylsiloxane) (Silicon Based Polymer Science: A Comprehensive Resource; Ziegler, J. M.; Fearson, F. W. G., Eds.; American Chemical Society: Washington, D.C., 1990). In addition, inclusion of an aromatic group has also been shown to increase the glass-transition temperatures for such polymers.

Besides thermal polymerization through the ethynyl (acetylene) units, the diethynylbenzene group is also amenable to both Diels-Alder and hydrosilylation reactions which result in crosslinked systems.

For the incorporation of an arylacetylene group in a PCSA-like system, several organic and catalytic transformations are currently available. Among them, three particularly simple and useful ones are: (i) the conversion of an ethynylbenzene into its dialkali salt and its subsequent conversion to the polymer with simultaneous elimination of the alkali metal halide; (ii) the conversion of an ethynylbenzene into its Grignard salt and its subsequent conversion to the polymer with simultaneous elimination of the alkaline metal dihalide; and (iii) the creation of an arylacetylene linker group by Sonogashira coupling reaction involving a diethynyl carboranylenesiloxane, carboranylenesilane or siloxane and a dihaloarene resulting in a polymer. The first two strategies involve the conversion of diethynylbenzene into a reactive bifunctional moiety by elimination of the ethynyl hydrogens.

Examples of polyarylacetylene polymers are depicted below. In these structures, suitable R groups include, but are not limited to, hydrogen, methyl, and phenyl. All the R groups may be the same, or there may be different R groups within the compound. For example, each silicon atom may have a hydrogen and either methyl or phenyl bound thereto. The m-carborane groups shown above (the unlabeled atoms are BH groups) may also be o-carborane, p-carborane, or other carborane groups having a different number of boron atoms. The m-phenylene group may also be o-phenylene or p-phenylene. Suitable values for m include, but are not limited to, 1, 2, 3, 4, and 5. Suitable values for p include, but are not limited to, 1, 2, 3, 4, 5, 6, 7, 8, and 9. Suitable values for n include, but are not limited to, at least 10, at least 100, and at least 1000.

The compounds may be made by reacting a Grignard reagent of diethynylbenzene or similarly reactive diethynylbenzene compound with the appropriate halo-terminated siloxane or silane compound according to the general formulae:

M may be Li, Na, K, or MgX', wherein X' is a halogen. X may be a halogen, such as F, Cl, Br, or I. The reaction may occur spontaneously at room temperature or below room temperature. The reactants may be provided in equimolar or near equimolar amounts to produce at least 10, 50, 100, or 1000 repeat units in the compound. Alternatively, one compound may be provided in excess to produce an oligomer terminated by the excess moiety. Compounds having a 2:1 ratio of arylacetylene to carboranylenesiloxane, carboranylenesilane, or siloxane are described below, but any ratio may be used. For example a 3:2 ratio of carboranylenesiloxane to arylacetylene would make the compound shown below.

Figure 1:
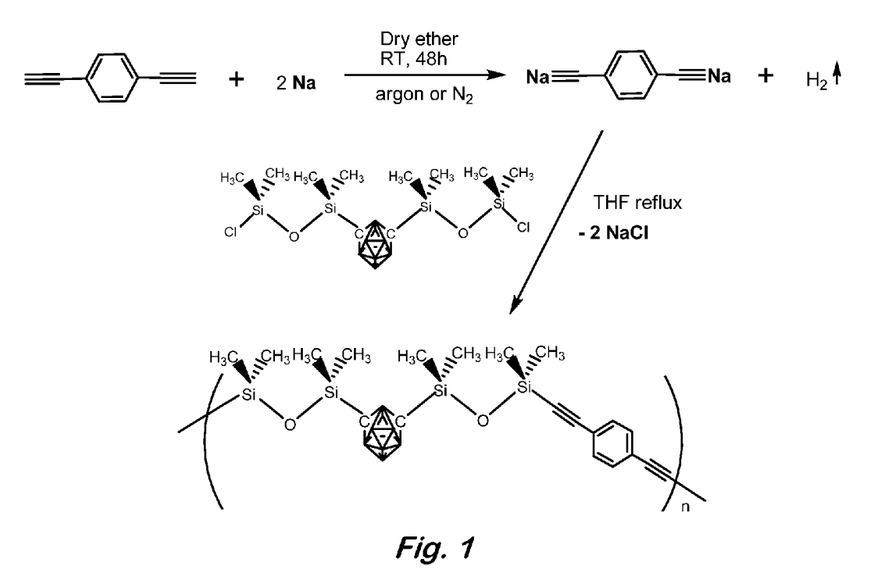
FIG. 1 shows a reaction strategy using a disodium salt for the production of polyarylacetylene polymer containing a carboranylenesiloxane. A similar strategy can also be utilized in the production of polyarylacetylene polymer containing either a carboranylenesilane or siloxane moiety.

By the first strategy, a diethynylbenzene (such as 1,4-diethynylbenzene) can be converted to its disodium salt by its reaction with sodium metal in dry ether solution in inert atmosphere (FIG. 1). The product is collected after two days of reaction subsequent to the liberation of $H_2$ gas (Shim, I. W.; Risen, Jr. W. M. *J. Organomet. Chem.* 1984, 260, 171-179). Such a disodium salt can be reacted with the corresponding dihalogen-terminated carboranylenesiloxane, carboranylenesilane, or siloxane in THF under room temperature to reflux conditions to form the linear polymer by the elimination of NaCl.

Figure 2:
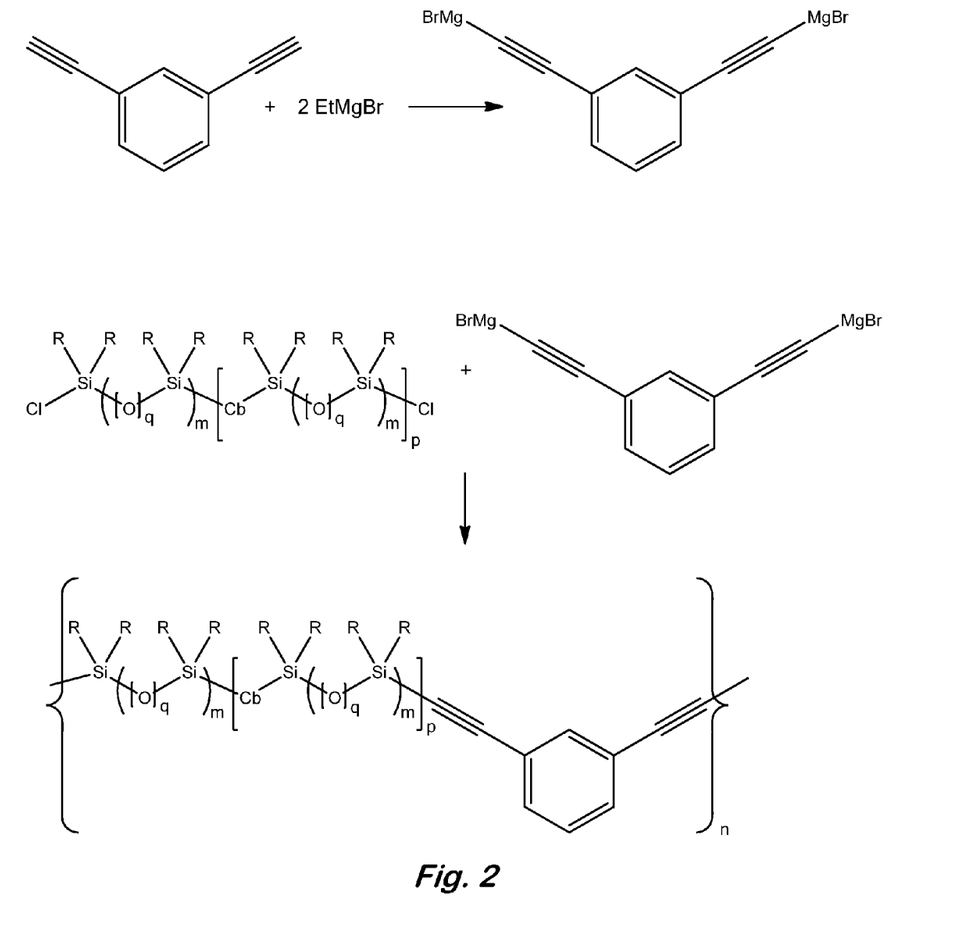
FIG. 2 shows a reaction strategy using a Grignard reagent for the production of polyarylacetylene polymer containing a carboranylenesiloxane.

By the second strategy, a diethynylbenzene can be converted into a Grignard reagent by reaction with ethylmagnesium bromide in THF (FIG. 2). Similar Grignard formation from 1,3-diethynylbenzene for producing polyacetylenes has been reported by the GE R&D Center in 1971 (White et al., *Macromolecules* 1971, 5(4), 526-531). Typically, this can be achieved under an inert atmosphere by heating the mixture between 80-90° C. for 2 h. For incorporation of the Grignard reagent into a linear polymer with a carboranylenesiloxane, a carboranylenesilane, or a siloxane moiety, the Grignard reagent is reacted with the corresponding dihalogen-terminated carboranylenesiloxane, carboranylenesilane, or siloxane in THF under room temperature to reflux conditions to form the linear polymer by the elimination of the Grignard salt (FIG. 2).

Figure 3:
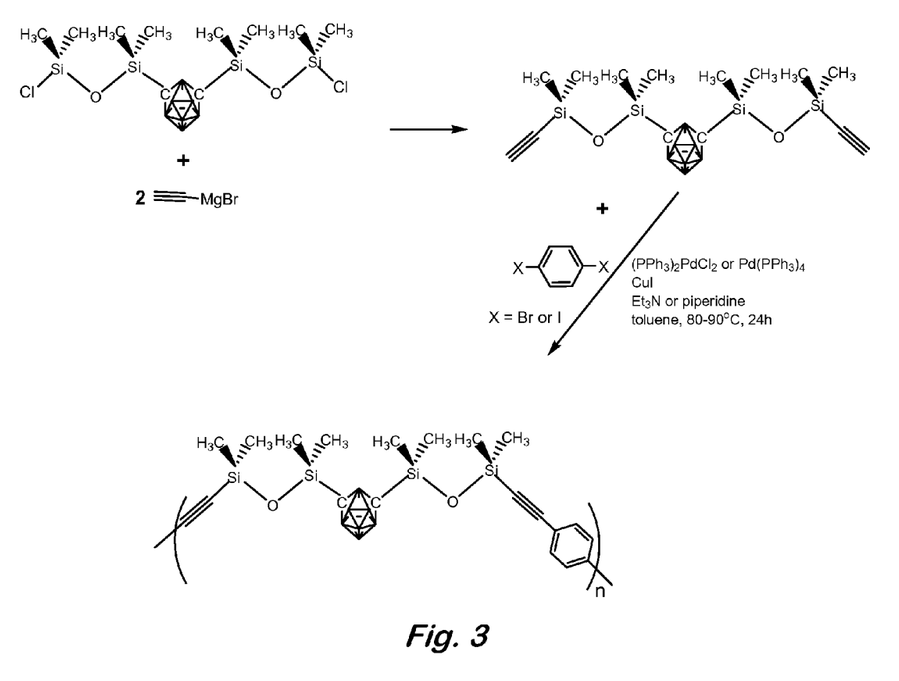
FIG. 3 shows a reaction strategy using a Sonogashira coupling reaction for the production of polyarylacetylene polymer containing a carboranylenesiloxane.

The third strategy utilizes metal-mediated catalytic reactions of a diethynyl-derivative of a carboranylenesiloxane, carboranylenesilane, or siloxane that may be reacted with a dihalogenated aromatic compound to produce the corresponding linear arylacetylene polymers. The most common catalytic reaction that is utilized is the Pd-catalyzed Sonogashira coupling reaction ((a) Sonogashira, In *Metal-Catalyzed Cross-Coupling Reactions*; Diederich, F., Stang, P. J., Eds.; Wiley-VCH: New York, 1998; Chapter 5. (b) Sonogashira, In *Comprehensive Organic Synthesis*; Trost, B. M., Ed.; Pergamon: New York, 1991; Vol. 3, Chapter 2.4). An example of such a transformation is shown in (FIG. 3) using the dichloro-terminated carboranylenesiloxane as the reactant. In the initial step, the carboranylenesiloxane monomer is converted into its diethynyl-terminated variant by reaction with ethynyl magnesium bromide. Subsequently, the product is The reactions of the compounds that produce the polyarylacetylene polymers may utilize equimolar quantities of the reactive arylacetylene component and the respective carboranylenesiloxane, carboranylenesilane, or siloxane component. Alternatively, if the reactions are performed at a ratio of 2:1 of arylacetylene:(carboranylenesiloxane, carboranylenesilane or siloxane) reactants, mainly monomers of the alkyne-terminated products can be produced which will be an important group of compounds in their own right. Examples of such compounds are shown below. Other ratios such as 3:2, 4:3, etc. may be used to form longer oligomers.

reacted with a dihalogenated arene under Sonogashira conditions to produce the corresponding carboranylenesiloxane arylacetylene polymer.

Utilizing the three discussed synthetic strategies, various polyarylacetylene polymers containing a carboranylenesiloxane, a carboranylenesilane or a siloxane moiety as shown above may be made. In the interest of not limiting the disclosure, it is to be assumed that all of the expressed examples may be arrived at by any one of the above elucidated reaction routes and by the interchangeable usage of any of the diethynylbenzene or dihaloarenes and any of the carboranylenesiloxane, carboranylenesilane or siloxane monomers. Some versions of the siloxane-containing polyarylacetylene polymers may also not contain any carborane groups.

Figure 4:
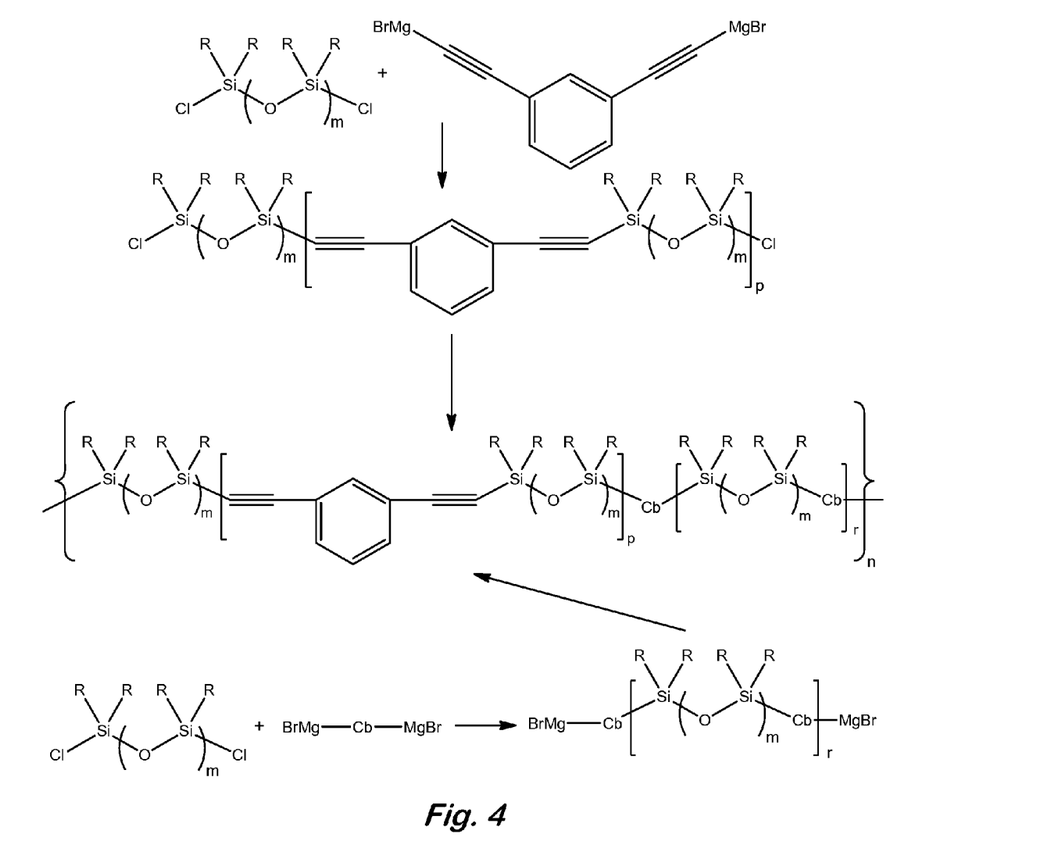
FIG. 4 shows formation of a block copolymer.

In another embodiment, block copolymers may be made by first reacting a diethynyl benzene with excess silane or siloxane according to the first and second strategy. In a separate, second reaction, the silane or siloxane is reacted with excess carborane, again according to the first and second strategy. The two oligomers are then reacted together to form a block copolymer. The scheme is shown in FIG. 4.

The option for curing by hydrosilylation and/or Diels-Alder (FIG. 5) reactions provides additional control over the curing temperature and a large processing window for composite and coating applications. The availability of the selection in the curing mechanisms will depend on the R groups that are present on the Si atoms in a particular polymer. In addition, there exists an option to use a cyclotrimerization catalyst to produce crosslinking aryl groups from the alkyne groups in the backbone of the polymers thereby yielding a greater flexibility in the curing conditions.

During the curing of the developed polymers, besides the option of thermal polymerization of the ethynyl component, the diethynylbenzene group, as a whole, should also be amenable to Diels-Alder reactions and hydrosilylation reactions (in cases where Si—H bond is available in proximity), both of which should result in the further enhancement of the crosslinking density in the cured networks.

In the polymers that lack a Si—H moiety, the curing will occur mainly by alkyne crosslinking or Diels-Alder type additions of the alkyne groups with the aryl moieties that result in the formation of new aryl rings which function as the focal points of the crosslinks. The cyclotrimerization of the alkyne groups which is a close variant of the Diels-Alder reaction, even though a possibility, may not be achieved under the proposed thermal conditions in the absence of a catalyst. However, the use of catalysts such as CpCo(PPH$_3$)$_2$, Cp*Co(C$_2$H$_4$)$_2$ or TaBr$_5$/Ph$_4$Sn during curing can result in the formation of aryl rings from such cyclotrimerizations (Agenet et al., *J. Am. Chem. Soc.* 2007, 129(28), 8860-8871). In the polymers that have Si—H bonds, the curing will occur by a combination of hydrosilylation and Diels-Alder reactions. It is likely that the hydrosilylations will occur at lower temperatures than the Diels-Alder additions and, hence, the type and extent of crosslinking in the disclosed systems can be dictated by the selection of the curing temperature, time, and external catalysts. The crosslinking in the disclosed polymers may also be affected by photochemical and radiation-induced means in addition to thermal and catalytic means.

The disclosed linear polymers containing carboranylenesiloxane, carboranylenesilane or siloxane, and arylacetylene moieties can yield networked systems with exceptional thermal and thermo-oxidative stabilities by reactions involving the acetylene groups. The networks should also have improved mechanical properties when compared to their diacetylene counterparts due to the presence of the phenyl ring in the backbone of the polymers. This opens up several applications for the materials such as in composites, coatings, elastomers, etc. The utilization of carboranylenesiloxane, carboranylenesilane and/or siloxane/silane moieties may provide a large palette of materials that can be produced with unique properties. Depending on the demands of the application, the versatility of the synthesis to incorporate various amounts of the carboranylenesiloxane, carboranylenesilane, siloxane, and silane groups within the linear oligomeric polymers is important to obtain the desired thermal and mechanical properties of the corresponding thermosets and ceramics.

The following examples are given to illustrate specific applications. These specific examples are not intended to limit the scope of the disclosure in this application.

EXAMPLE 1

Synthesis of a polyarylacetylene from a dichloro-terminated carboranylenesiloxane and the disodium derivative of 1,4-diethynylbenzene by the alkali halide elimination route—A flame-dried 250 mL Schlenk flask under argon was charged with 50 mL of dry ether under argon. Sodium metal (0.92 g, 40 mmol) was added to the flask which was followed by the gradual addition of 1,4-diethynylbenzene (2.52 g, 20 mmol). The mixture was stirred for 48 h at room temperature. The evolved H$_2$ gas was released frequently through the vacuum line by reducing or stopping the flow of argon. The dark grey precipitate was filtered, washed with ether, dried, and collected under argon. The precipitate was taken as a dispersion in 50 mL of dry THF and 1,7-bis(chlorotetramethyldisiloxyl)-m-carborane (8.64 mL, 9.55 g, 20 mmol) was added in 40 min. The solution was refluxed overnight resulting in the production of a pale orange solution. The mixture was cooled to RT. To this mixture, 0.3 mL of 1,7-bis(chlorotetramethyldisiloxyl)-m-carborane was added dropwise and the mixture was refluxed overnight. The mixture was transferred to a cold aqueous NH$_4$Cl solution resulting in an orange-yellow solution and dissolution of NaCl. The pH of the mixture was adjusted to 7 using 1 M HCl. The product was extracted by washing with several batches of diethyl ether in a separatory funnel. Subsequently, the ether extracts were dried over MgSO$_4$, filtered through a pad of Celite and concentrated in vacuo. A pale yellow/orange product was obtained in 98% yield.

Spectroscopic characterizations: IR (NaCl disk, cm$^{-1}$): 2956 ($v_{C—H}$, Si—CH$_3$), 2599 ($v_{B—H}$), 2155 ($v_{C≡C}$), 1401 ($v_{—CH2\ bend}$), 1259 ($v_{Si—C}$), 1074 ($v_{Si—O}$). $^1$H NMR (CDCl$_3$, ppm): 0.281 (Si—CH$_3$), 0.344 (Si—CH$_3$), 7.431 (—C$_6$H$_4$). $^{13}$C{$^1$H} NMR (CDCl$_3$, ppm): 0.822 (Si—CH$_3$), 2.246 (Si—CH$_3$), 68.504 (m-C$_2$B$_{10}$H$_{10}$), 93.849 (—C≡C—), 103.342 (—C≡C—), 123.141 (p-C$_6$H$_4$), 132.378 (p-C$_6$H$_4$).

Thermal characterizations: The TGA/DTA and DSC thermograms of the product were performed in N$_2$. TGA: Degradation temperature or temperature at 5% weight loss of the polymer=505° C. % Weight retention at 1000° C. in N$_2$=85%. % Weight retention at 1000° C. in air=93%.

DSC: Exotherms at 298° C. and 398° C., corresponding to the curing of the terminal acetylene and internal acetylene groups, respectively, by Diels-Alder reaction.

EXAMPLE 2

Synthesis of a polyarylacetylene from a dichloro-terminated carboranylenesiloxane and the disodium derivative of 1,3-diethynylbenzene by the Grignard route—A flame-dried 250 mL Schlenk flask under argon was charged with 40 mL of 1.0 M solution of ethylmagnesium bromide solution in THF (40 mmol). 1,3-Diethynylbenzene (2.64 mL, 2.51 g, 20 mmol) was added to the solution dropwise over a period of 40 minutes. The solution was heated to 80° C. and the heating was continued for 1.5 h resulting in the formation of a green-grey precipitate/suspension. The suspension became white in appearance when the solution was heated at 90° C. for an additional 45 min. The solution was then cooled to RT and 1,7-bis(chlorotetramethyldisiloxyl)-m-carborane (8.64 mL, 9.55 g, 20 mmol) was added in 40 min. 5 mL of THF was also added to the mixture at this point. The solution was refluxed for an hour causing the dissolution of the white precipitate and the production of a pale orange solution. The mixture was stirred overnight at RT. To this mixture, 0.3 mL of 1,7-bis(chlorotetramethyldisiloxyl)-m-carborane was added dropwise and the mixture was stirred at RT for an hour. The mixture was transferred to a cold aqueous NH$_4$Cl solution resulting in a yellow solution and copious amount of a white precipitate (MgBrCl). The pH of the mixture was adjusted to 7 using 1 M HCl. The product was extracted by washing with several batches of diethyl ether in a separatory funnel. Subsequently, the ether extracts were dried over MgSO$_4$, filtered through a pad of Celite, and concentrated in vacuo. A pale yellow/orange product was obtained in 98% yield.

Spectroscopic characterizations: IR (NaCl disk, cm$^{-1}$): 2955 ($v_{C—H}$, Si—CH$_3$), 2598 ($v_{B—H}$), 2152 ($v_{C≡C}$), 1402 ($v_{—CH2\ bend}$), 1257 ($v_{Si—C}$), 1076 ($v_{Si—O}$). $^1$H NMR (CDCl$_3$, ppm): 0.283 (Si—CH$_3$), 0.342 (Si—CH$_3$), 7.289 (—C$_6$H$_4$), 7.433 (—C$_6$H$_4$), 7.59 (—C$_6$H$_4$). $^{13}$C{$^1$H} NMR (CDCl$_3$, ppm): 0.824 (Si—CH$_3$), 2.248 (Si—CH$_3$), 68.501 (m-C$_2$B$_{10}$H$_{10}$), 93.851 (—C≡C—), 103.346 (—C≡C—), 123.133 (m-C$_6$H$_4$), 128.587 (m-C$_6$H$_4$), 132.380 (m-C$_6$H$_4$), 135.601 (m-C$_6$H$_4$).

Figure 6:
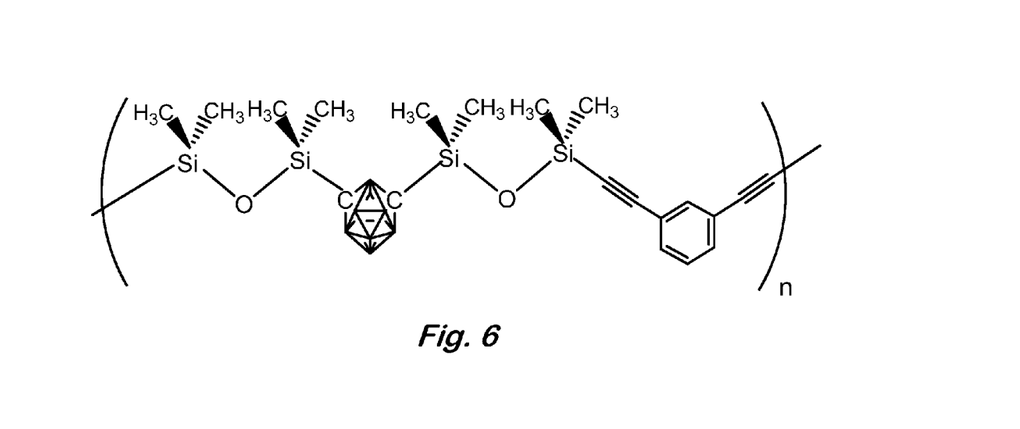
FIG. 6 shows a representative carboranylenesiloxane-containing polyarylacetylene.
Figure 7:
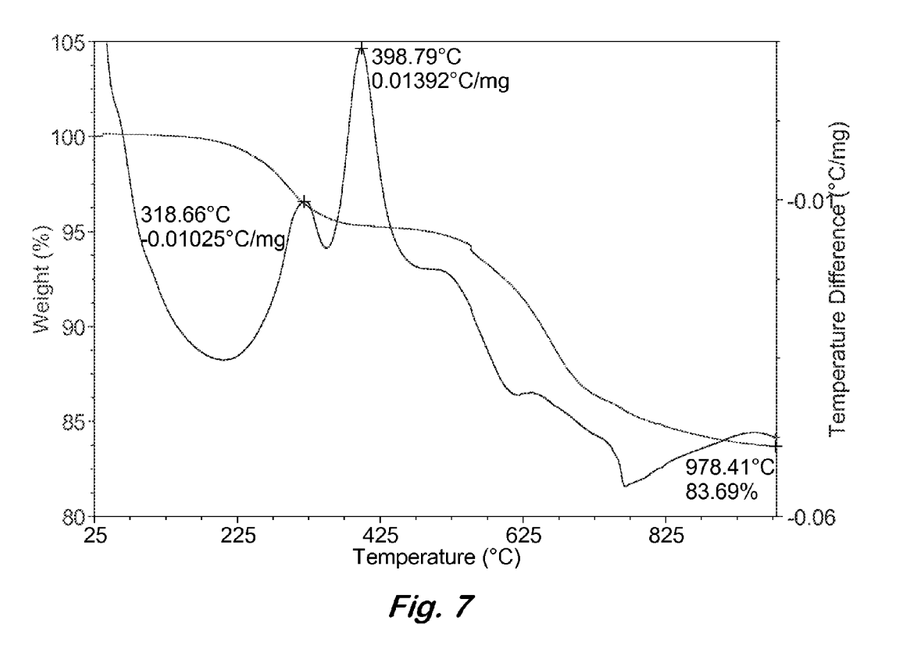
FIG. 7 shows a TGA/DTA thermogram of the compound of FIG. 6.
Figure 8:
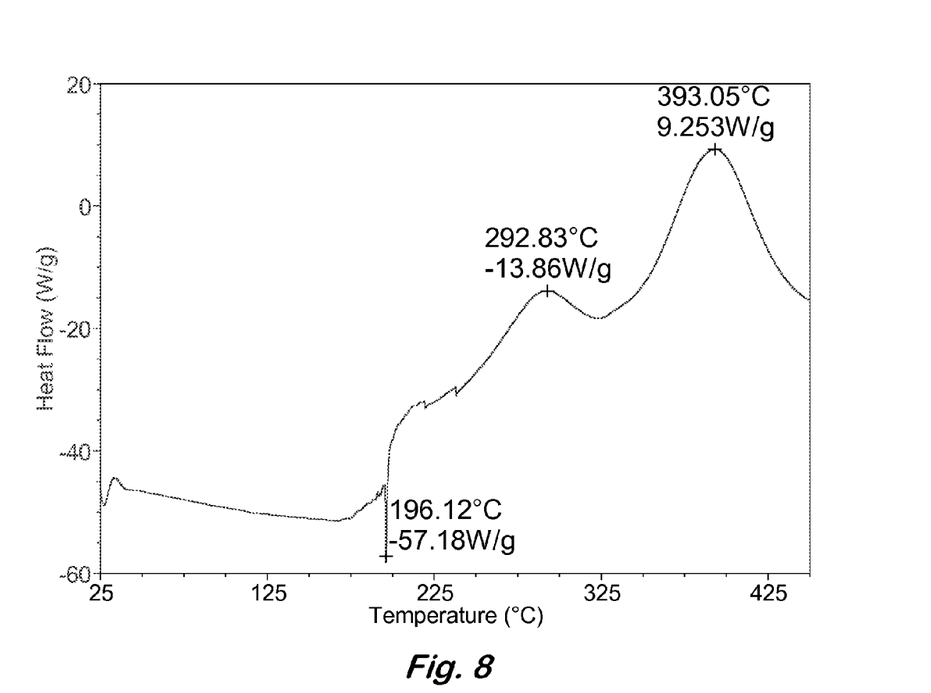
FIG. 8 shows a DSC thermogram of the compound of FIG. 6.

Thermal characterizations: The TGA/DTA (FIG. 7) and DSC (FIG. 8) thermograms in N$_2$ of a representative carboranylenesiloxane-containing polyarylacetylene (FIG. 6) were performed.

TGA: Degradation temperature or temperature at 5% weight loss of the polymer ($T_{d,5}$)=491° C. % Weight retention at 1000° C. in N$_2$=84%. % Weight retention at 1000° C. in air=92%.

DSC: Exotherms: At 293° C. and 393° C., corresponding to the curing of the terminal acetylene and internal acetylene groups, respectively, by Diels-Alder reaction.

Figure 5:
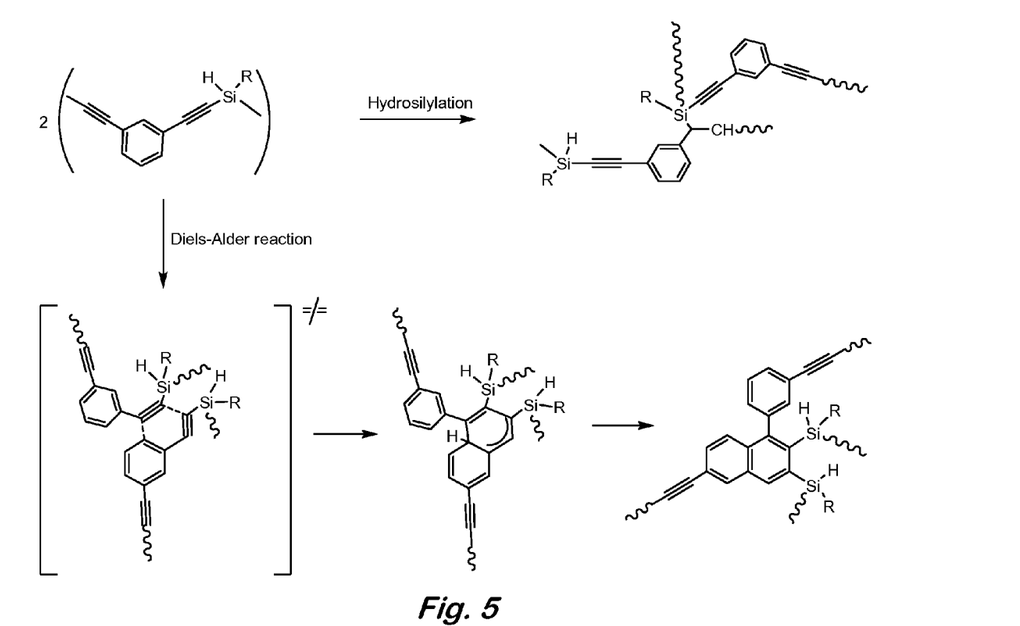
FIG. 5 shows curing pathways such as hydrosilylation and Diels-Alder reactions that are available for the produced polyarylacetylenes.

Curing mechanisms in the developed polyarylacetylene polymers: The disclosed linear oligomeric polymers are viscous liquids at room temperature. They can be converted to networked or crosslinked thermosets by thermal polymerization of the polymers in the range 250-450° C. The curing pathways such as Diels-Alder reaction and hydrosilylation reactions that are available for the ethynylbenzene groups during the production of crosslinked polyarylacetylenes are shown in FIG. 5 (Kuroki et al., *Macromolecules* 1998, 31, 2804-2808).

EXAMPLE 3

Synthesis of the polyarylacetylene containing a carboranylenesiloxane by Pd-catalyzed Sonagashira coupling reaction—To initiate the Pd-catalyzed Sonagashira coupling reaction, the carboranylenesiloxane monomer, 1,7-bis(chlorotetramethyldisiloxyl)-m-carborane, was initially converted to 1,7-bis(ethynyltetramethyldisiloxyl)-m-carborane by reaction with ethynylmagnesium bromide as follows:

A 250 mL Schlenk flask containing 1,7-bis(chlorotetramethyldisiloxyl)-m-carborane (15.81 g, 33.11 mmol) in 30 mL THF under argon was cooled in an ice bath. The solution was then treated with 133 mL of 0.5 M ethynylmagnesium bromide (66.5 mmol) which was slowly added via syringe at 0° C. The cold bath was removed and the resulting solution was allowed to stir at room temperature for two hours. The reaction was quenched by addition of $Me_3SiCl$ (2-3 mL) and the organics removed by aqueous extraction with diethyl ether and dried over $MgSO_4$.

Spectroscopic characterizations: IR (NaCl disk, $cm^{-1}$): 3290 ($v_{C-H}$, —$C_2H$), (2964 ($v_{C-H}$, Si—$CH_3$), 2596 ($v_{B-H}$), 2039 ($v_{C\equiv C}$), 1260 ($v_{Si-C}$), 1080 ($v_{Si-O}$), 798 (Si—C bend). $^1H$ NMR ($CDCl_3$, ppm): 0.23 (Si—$CH_3$), 0.27 (Si—$CH_3$), 2.41 (—$C_2H$). $^{13}C\{^1H\}$ NMR ($CDCl_3$, ppm): 0.25 (Si—$CH_3$), 1.89 (Si—$CH_3$), 68.15 (m-$C_2B_{10}H_{10}$), 88.58 (—C≡CH), 92.64 (—C≡CH).

The produced 1,7-bis(ethynyltetramethyldisiloxyl)-m-carborane was converted to the polyarylacetylene by the following procedure.

Sonogashira coupling reaction of 1,7-bis(ethynyltetramethyldisiloxyl)-m-carborane with 1,4-diodobenzene: In a 250 mL Schlenk flask, a mixture of 1,7-bis(ethynyltetramethyldisiloxyl)-m-carborane (9.22 g, 20 mmol), 1,4-diodobenzene (6.46 g, 20 mmol), $(PPh_3)_2PdCl_2$ (0.02 g, 0.028 mmol), CuI (0.086 g, 0.450 mmol) and $PPh_3$ (0.20 g, 0.762 mmol) in triethylamine (60 mL) and toluene (60 mL) was degassed and stirred under $N_2$ at 90° C. for 16 h. A white precipitate began to appear in the initial colorless solution after 30 min and the solution became more and more intensely yellow and then orange over the next hour. After 24 h, the reaction mixture was orange in color. The product was extracted by washing with several batches of diethyl ether in a separatory funnel. Subsequently, the ether extracts were dried over $MgSO_4$, filtered through a pad of Celite and concentrated in vacuo. A pale yellow/orange product was obtained in 99% yield.

Spectroscopic characterizations: IR (NaCl disk, $cm^{-1}$): 2956 ($v_{C-H}$, Si—$CH_3$), 2599 ($v_{B-H}$), 2155 ($v_{C\equiv C}$), 1401 ($v_{-CH2\ bend}$), 1259 ($v_{Si-C}$), 1074 ($v_{Si-O}$). $^1H$ NMR ($CDCl_3$, ppm): 0.281 (Si—$CH_3$), 0.344 (Si—$CH_3$), 7.431 (—$C_6H_4$). $^{13}C\{^1H\}$ NMR ($CDCl_3$, ppm): 0.822 (Si—$CH_3$), 2.246 (Si—$CH_3$), 68.504 (m-$C_2B_{10}H_{10}$), 93.849 (—C≡C—), 103.342 (—C≡C—), 123.141 (p-$C_6H_4$), 132.378 (p-$C_6H_4$).

EXAMPLE 4

Synthesis of the polyarylacetylene containing carboranylenesiloxane with various carborane:siloxane:arylacetylene ratios and different component siloxanes by the Grignard route—Alternating copolymer with siloxane-carborane-arylacetylene ratio of 3:2:1: (Prophetic) Flask #1: A 250 mL Schlenk is charged with m-carborane (0.57 g, 3.95 mmol) and 1 mL of dry THF. The mixture is placed in an ice bath and 2.5 M n-butyl lithium in hexanes (3.19 mL, 7.98 mmol) is added dropwise via a syringe. After complete addition, the ice bath is removed. After stirring overnight, volatiles are removed with high vacuum and the solid residue is dissolved in fresh THF (5 mL). This solution is then cooled with an ice bath and the corresponding 1,3-dichlorotetramethyldisiloxane, 1,5-dichlorohexamethyltrisiloxane, 1,7-dichlorooctamethyltetrasiloxane or 1,9-dichlorodecamethylpentasiloxane (5.92 mmol) is added dropwise. A white precipitate is expected to be formed very quickly. The ice bath is removed and the reaction is allowed to proceed for about 5 h.

Flask #2: A 50 mL Schlenk flask is charged with 3.95 mL of 1.0 M solution of ethylmagnesium bromide solution in THF (3.95 mmol). 1,3-Diethynylbenzene (0.26 mL, 1.98 mmol) is added to the solution dropwise over a period of 15 minutes. The solution is heated to 80° C. and the heating is continued for 1.5 h, expected to result in formation of a green-grey precipitate/suspension. The suspension is expected to become white in appearance when the solution is heated at 90° C. for an additional 45 min.

Chain extension: The contents of flask #2 are then cannulated into flask #1 using a double-tipped needle. Following the transfer, the remaining contents of flask #2 are rinsed three times with THF (4 mL/rinse) through the cannula into flask #1. The solution is refluxed for an hour, expected to cause the dissolution of the white precipitate and the production of a pale orange solution. The mixture is stirred overnight at RT. The mixture is transferred to a cold aqueous $NH_4Cl$ solution, expected to result in a yellow solution and copious amount of a white precipitate (MgBrCl). The pH of the mixture is adjusted to 7 using 1 M HCl. The product is extracted by washing with several batches of diethyl ether in a separatory funnel. Subsequently, the ether extracts are dried over $MgSO_4$, filtered through a pad of Celite, and concentrated in vacuo. A pale yellow/orange product is expected to be obtained.

EXAMPLE 5

Synthesis of the polyarylacetylene containing carboranylenesiloxane with various carborane:siloxane:arylacetylene ratios and different component siloxanes by the Grignard route—Block copolymer with siloxane-carborane-arylacetylene ratio of 3:2:1—(Prophetic) Flask #1 involves production of siloxane-arylacetylene blocks with an average degree of polymerization of 3. A 50 ml, Schlenk flask is charged with 7.9 mL of 1.0 M solution of ethylmagnesium bromide solution in THF (7.90 mmol). 1,3-Diethynylbenzene (0.52 mL, 3.95 mmol) is added to the solution dropwise over a period of 15 minutes. The solution is heated to 80° C. and the heating is continued for 1.5 h, expected to result in formation of a green-grey precipitate/suspension. The suspension is expected to become white in appearance when the solution is heated at 90° C. for an additional 45 min. The mixture is cooled to RT and the corresponding siloxane (1,3-dichlorotetramethyldisiloxane, 1,5-dichlorohexamethyltrisiloxane, 1,7-dichlorooctamethyltetrasiloxane, or 1,9-dichlorodecamethylpentasiloxane: 7.90 mmol) is added dropwise. The mixture is refluxed for an hour.

Flask #2 involves production of carborane-siloxane blocks of varying degrees of polymerization. In a 250-mL flame-dried Schlenk flask under argon, m-carborane (1.14 g, 7.90 mmol) is dissolved in 1 mL of THF and is placed in an ice bath. n-Butyl lithium in hexanes (2.5 M, 6.32 mL, 15.8 mmol) is added dropwise to the solution. The mixture is warmed to room temperature and the volatiles are then removed under vacuum. The residue is dissolved in 2 mL of THF and the mixture is cooled to 0° C. To this solution, the corresponding siloxane (1,3-dichlorotetramethyldisiloxane, 1,5-dichlorohexamethyltrisiloxane, 1,7-dichlorooctamethyltetrasiloxane, or 1,9-dichlorodecamethylpentasiloxane: 3.95 mmol) is added dropwise via a gastight syringe. The resulting mixture is stirred for 3 h at room temperature.

Chain extension: The contents of flask #1 are cannulated into flask #2 and the mixture is stirred for 16 h. The mixture is then poured into 50 mL of a cold, saturated $NH_4Cl$ solution and extracted three times with 75 mL each of $Et_2O$. The $Et_2O$ extracts are combined, washed with 100 mL of brine, dried over anhydrous Na$_2$SO$_4$, filtered through a 1-in. pad of Celite, and the solvent removed under vacuum. A pale orange viscous oil is expected to be obtained.

EXAMPLE 6

Synthesis of the polyarylacetylene containing carboranylenesiloxane with various carborane:siloxane:arylacetylene ratios and different component siloxanes by the Grignard route—Alternating copolymer with siloxane-carborane-arylacetylene ratio of 5:4:1: (Prophetic) A similar procedure as with the alternating copolymer with siloxane:carborane:arylacetylene ratio of 3:2:1 described in Example 4 is used for the synthesis of the alternating polymer with a 5:4:1 ratio, except that the stoichiometric ratios of the corresponding siloxane:arylacetylene and carborane:arylacetylene are 5:1 and 4:1, respectively.

EXAMPLE 7

Synthesis of the polyarylacetylene containing carboranylenesiloxane with various carborane:siloxane:arylacetylene ratios and different component siloxanes by the Grignard route—Alternating copolymer with siloxane-carborane-arylacetylene ratio of 10:9:1: (Prophetic) A similar procedure as with the alternating copolymer with siloxane:carborane:arylacetylene ratio of 3:2:1 described in Example 4 is used for the synthesis of the alternating polymer with a 10:9:1 ratio, except that the stoichiometric ratios of the corresponding siloxane:arylacetylene and carborane:arylacetylene are 10:1 and 9:1, respectively.

EXAMPLE 8

Synthesis of the polyarylacetylene containing carboranylenesiloxane of 1,3-dichloro-1,3-diphenyl-1,3-dimethyl disiloxane with various carborane:siloxane:arylacetylene ratios by the Grignard route—Alternating copolymer with siloxane-carborane-arylacetylene ratio of 3:2:1: (Prophetic) Flask #1: A 250 mL Schlenk is charged with m-carborane (0.57 g, 3.95 mmol) and 1 mL of dry THF. The mixture is placed in an ice bath and 2.5 M n-butyl lithium in hexanes (3.19 mL, 7.98 mmol) is added dropwise via a syringe. After complete addition, the ice bath is removed. After stirring overnight, volatiles are removed with high vacuum and the solid residue is dissolved in fresh THF (5 mL). This solution wisas then cooled with an ice bath and 1,3-dichloro-1,3-diphenyl-1,3-dimethyl disiloxane (M.W.=327.36 g/mol, 1.938 g, 5.92 mmol) is added dropwise. A white precipitate is expected to be formed very quickly. The ice bath is removed and the reaction is allowed to proceed for about 5 h.

Flask #2: A 50 mL Schlenk flask is charged with 3.95 mL of 1.0 M solution of ethylmagnesium bromide solution in THF (3.95 mmol). 1,3-Diethynylbenzene (0.26 mL, 1.98 mmol) is added to the solution dropwise over a period of 15 minutes. The solution is heated to 80° C. and the heating is continued for 1.5 h, expected to result in formation of a green-grey precipitate/suspension. The suspension is expected to become white in appearance when the solution is heated at 90° C. for an additional 45 min.

Chain extension: The contents of flask #2 are then cannulated into flask #1 using a double-tipped needle. Following the transfer, the remaining contents of flask #2 are rinsed three times with THF (4 mL/rinse) through the cannula into flask #1. The solution is refluxed for an hour, expected to cause the dissolution of the white precipitate and the production of a pale orange solution. The mixture is stirred overnight at RT. The mixture is transferred to a cold aqueous NH$_4$Cl solution, expected to result in a yellow solution and copious amount of a white precipitate (MgBrCl). The pH of the mixture is adjusted to 7 using 1 M HCl. The product is extracted by washing with several batches of diethyl ether in a separatory funnel. Subsequently, the ether extracts are dried over MgSO$_4$, filtered through a pad of Celite, and concentrated in vacuo. A pale yellow/orange product is expected to be obtained.

EXAMPLE 9

Synthesis of the polyarylacetylene containing carboranylenesiloxane of 1,3-dichloro-1,3-diphenyl-1,3-dimethyl disiloxane with various carborane:siloxane:arylacetylene ratios by the Grignard route—Block copolymer with siloxane-carborane-arylacetylene ratio of 3:2:1: (Prophetic) Flask #1 involves production of siloxane-arylacetylene blocks with an average degree of polymerization of 3. A 50 mL Schlenk flask is charged with 7.9 mL of 1.0 M solution of ethylmagnesium bromide solution in THF (7.90 mmol). 1,3-Diethynylbenzene (0.52 mL, 3.95 mmol) is added to the solution dropwise over a period of 15 minutes. The solution is heated to 80° C. and the heating is continued for 1.5 h, expected to result in formation of a green-grey precipitate/suspension. The suspension is expected to become white in appearance when the solution is heated at 90° C. for the next 45 min. The mixture is cooled to RT and 1,3-dichloro-1,3-diphenyl-1,3-dimethyl disiloxane (M.W.=327.36 g/mol, 2.586 g, 7.90 mmol) is added dropwise. The mixture is refluxed for an hour.

Flask #2 involves production of carborane-siloxane blocks of varying degrees of polymerization. In a 250-mL flame-dried Schlenk flask under argon, m-carborane (1.14 g, 7.90 mmol) is dissolved in 1 mL of THF and is placed in an ice bath. n-Butyllithium in hexanes (2.5 M, 6.32 mL, 15.8 mmol) is added dropwise to the solution. The mixture is warmed to room temperature and the volatiles are then removed under vacuum. The residue is dissolved in 2 mL of THF and the mixture is cooled to 0° C. To this solution, 1,3-dichloro-1,3-diphenyl-1,3-dimethyl disiloxane (M.W.=327.36 g/mol, 1.293 g, 3.95 mmol) is added dropwise via a gastight syringe. The resulting mixture is stirred for 3 h at room temperature.

Chain extension: The contents of flask #1 are cannulated into flask #2 and the mixture is stirred for 16 h. The mixture is then poured into 50 mL of a cold, saturated NH$_4$Cl solution and extracted three times with 75 mL each of Et$_2$O. The Et$_2$O extracts are combined, washed with 100 mL of brine, dried over anhydrous Na$_2$SO$_4$, filtered through a 1-in. pad of Celite, and the solvent is removed under vacuum. A pale orange viscous oil is expected to be obtained.

EXAMPLE 10

Synthesis of the polyarylacetylene containing carboranylenesiloxane of 1,3-dichloro-1,3-diphenyl-1,3-dimethyl disiloxane with various carborane:siloxane:arylacetylene ratios by the Grignard route—Alternating copolymer with siloxane-carborane-arylacetylene ratio of 5:4:1: (Prophetic) A similar procedure as with the alternating copolymer with siloxane:carborane:arylacetylene ratio of 3:2:1 as described in Example 8 is used for the synthesis of the alternating copolymer with a 5:4:1 ratio, except that the stoichiometric ratios of 1,3-dichloro-1,3-diphenyl-1,3-dimethyl disiloxane:arylacetylene and carborane:arylacetylene are 5:1 and 4:1, respectively.

EXAMPLE 11

Synthesis of the polyarylacetylene containing carboranylenesiloxane of 1,3-dichloro-1,3-diphenyl-1,3-dimethyl disiloxane with various carborane:siloxane:arylacetylene ratios by the Grignard route—Alternating copolymer with siloxane-carborane-arylacetylene ratio of 10:9:1: (Prophetic) A similar procedure as with the alternating copolymer with siloxane:carborane:arylacetylene ratio of 3:2:1 as described in Example 8 is used for the synthesis of the alternating copolymer with a 10:9:1 ratio, except that the stoichiometric ratios of 1,3-dichloro-1,3-diphenyl-1,3-dimethyl disiloxane: arylacetylene and carborane:arylacetylene are 10:1 and 9:1, respectively.

EXAMPLE 12

Synthesis of the polyarylacetylene containing carboranylenesiloxane of 1,3-dichloro-tetraphenyl disiloxane with various carborane:siloxane:arylacetylene ratios by the Grignard route—Alternating copolymer with siloxane-carborane-arylacetylene ratio of 3:2:1: (Prophetic) Flask #1: A 250 mL Schlenk is charged with m-carborane (0.57 g, 3.95 mmol) and 1 mL of dry THF. The mixture is placed in an ice bath and 2.5 M n-butyl lithium in hexanes (3.19 mL, 7.98 mmol) is added dropwise via a syringe. After complete addition, the ice bath is removed. After stirring overnight, volatiles are removed with high vacuum and the solid residue is dissolved in fresh THF (5 mL). This solution is then cooled with an ice bath and 1,3-dichloro-tetraphenyl disiloxane (M.W.=451.50 g/mol, 2.672 g, 5.92 mmol) is added dropwise. A white precipitate is expected to be formed very quickly. The ice bath is removed and the reaction is allowed to proceed for about 5 h.

Flask #2: A 50 mL Schlenk flask is charged with 3.95 mL of 1.0 M solution of ethylmagnesium bromide solution in THF (3.95 mmol). 1,3-Diethynylbenzene (0.26 mL, 1.98 mmol) is added to the solution dropwise over a period of 15 minutes. The solution is heated to 80° C. and the heating is continued for 1.5 h, expected to result in formation of a green-grey precipitate/suspension. The suspension is expected to become white in appearance when the solution is heated at 90° C. for an additional 45 min.

Chain extension: The contents of flask #2 are then cannulated into flask #1 using a double-tipped needle. Following the transfer, the remaining contents of flask #2 are rinsed three times with THF (4 mL/rinse) through the cannula into flask #1. The solution is refluxed for an hour, expected to cause the dissolution of the white precipitate and the production of a pale orange solution. The mixture is stirred overnight at RT. The mixture is transferred to a cold aqueous $NH_4Cl$ solution expected to result in a yellow solution and copious amount of a white precipitate (MgBrCl). The pH of the mixture is adjusted to 7 using 1 M HCl. The product is extracted by washing with several batches of diethyl ether in a separatory funnel. Subsequently, the ether extracts are dried over $MgSO_4$, filtered through a pad of Celite, and concentrated in vacuo. A pale yellow/orange product is expected to be obtained.

EXAMPLE 13

Synthesis of the polyarylacetylene containing carboranylenesiloxane of 1,3-dichloro-tetraphenyl disiloxane with various carborane:siloxane:arylacetylene ratios by the Grignard route—Block copolymer with siloxane-carborane-arylacetylene ratio of 3:2:1: (Prophetic) Flask #1 involves production of siloxane-arylacetylene blocks with an average degree of polymerization of 3. A 50 mL Schlenk flask is charged with 7.9 mL of 1.0 M solution of ethylmagnesium bromide solution in THF (7.90 mmol). 1,3-Diethynylbenzene (0.52 mL, 3.95 mmol) is added to the solution dropwise over a period of 15 minutes. The solution is heated to 80° C. and the heating is continued for 1.5 h, expected to result in formation of a green-grey precipitate/suspension. The suspension is expected to become white in appearance when the solution is heated at 90° C. for an additional 45 min. The mixture is cooled to RT and 1,3-dichloro-tetraphenyl disiloxane (M.W.=451.50 g/mol, 3.566 g, 7.90 mmol) is added dropwise. The mixture is refluxed for an hour.

Flask #2 involves production of carborane-siloxane blocks of varying degrees of polymerization. In a 250-mL flame-dried Schlenk flask under argon, m-carborane (1.14 g, 7.90 mmol) is dissolved in 1 mL of THF and is placed in an ice bath. n-Butyllithium in hexanes (2.5 M, 6.32 mL, 15.8 mmol) is added dropwise to the solution. The mixture is warmed to room temperature and the volatiles are then removed under vacuum. The residue is dissolved in 2 mL of THF and the mixture is cooled to 0° C. To this solution, 1,3-dichloro-tetraphenyl disiloxane (M.W.=451.50 g/mol, 1.783 g, 3.95 mmol) is added dropwise via a gastight syringe. The resulting mixture is stirred for 3 h at room temperature.

Chain extension: The contents of flask #1 are cannulated into flask #2 and the mixture is stirred for 16 h. The mixture is then poured into 50 mL of a cold, saturated $NH_4Cl$ solution and extracted three times with 75 mL each of $Et_2O$. The $Et_2O$ extracts are combined, washed with 100 mL of brine, dried over anhydrous $Na_2SO_4$, filtered through a 1-in. pad of Celite, and the solvent is removed under vacuum. A pale orange viscous oil was is expected to be obtained.

EXAMPLE 14

Synthesis of the polyarylacetylene containing carboranylenesiloxane of 1,3-dichloro-tetraphenyl disiloxane with various carborane:siloxane:arylacetylene ratios by the Grignard route—Alternating copolymer with siloxane-carborane-arylacetylene ratio of 5:4:1: (Prophetic) A similar procedure as with the alternating copolymer with siloxane:carborane: arylacetylene ratio of 3:2:1 as described in Example 12 is used for the synthesis of the alternating copolymer with a 5:4:1 ratio, except that the stoichiometric ratios of 1,3-dichloro-tetraphenyl disiloxane:arylacetylene and carborane: arylacetylene are 5:1 and 4:1, respectively.

EXAMPLE 15

Synthesis of the polyarylacetylene containing carboranylenesiloxane of 1,3-dichloro-tetraphenyl disiloxane with various carborane:siloxane:arylacetylene ratios by the Grignard route—Alternating copolymer with siloxane-carborane-arylacetylene ratio of 10:9:1: (Prophetic) A similar procedure as with the alternating copolymer with siloxane:carborane: arylacetylene ratio of 3:2:1 as described in Example 12 is used for the synthesis of the alternating copolymer with a 10:9:1 ratio, except that the stoichiometric ratios of 1,3-dichloro-tetraphenyl disiloxane:arylacetylene and carborane: arylacetylene are 10:1 and 9:1, respectively.

EXAMPLE 16

Synthesis of the polyarylacetylene containing 1,2-dichlorotetramethyldisilane by the Grignard route—Flask # 1: A flame-dried 100 mL Schlenk flask under argon was charged with 20 mL of 1.0 M solution of ethylmagnesium bromide solution in THF (F.W.=133.27, 20 mmol). 1,4-Diethynylbenzene (1.32 mL, 10 mmol, F.W.=126.15, d=0.949) was added to the solution dropwise over a period of 40 minutes. The solution was heated to 80° C. and the heating was continued for 1.5 h resulting in the formation of a green-grey precipitate/ suspension. The suspension became white in appearance when the solution was heated at 90° C. for the next 45 min. The solution was then cooled to RT.

Flask #2: In a 100-mL flame-dried Schlenk flask under argon, m-carborane (1.44 g, 10 mmol) was dissolved in 5 mL of THF and was placed in an ice bath. n-Butyllithium in hexanes (2.5 M, 8 mL, 20 mmol) was added dropwise to the solution. The mixture was warmed to room temperature and the volatiles were then removed under vacuum. The residue was dissolved in 2 mL of THF and the mixture was cooled to 0° C. To this solution, 1,2-dichlorotetramethyldisilane (M.W.=187.20 g/mol, 3.73 mL, 3.75 g, 20 mmol) was added dropwise via a gastight syringe. The resulting mixture was stirred for 3 h at room temperature.

Chain extension: The contents of flask #1 were cannulated into flask #2 and the mixture was stirred for 16 h. The mixture was then poured into 50 mL of a cold, saturated NH$_4$Cl solution and extracted three times with 75 mL each of Et$_2$O. The Et$_2$O extracts were combined, washed with 100 mL of brine, dried over anhydrous Na$_2$SO$_4$, filtered through a 1-in. pad of Celite, and the solvent was removed under vacuum. A pale orange viscous oil was obtained (98% yield).

Spectroscopic characterizations: IR (NaCl disk, cm$^{-1}$): 2951 ($v_{C-H}$, Si—CH$_3$), 2152 ($v_{C\equiv C}$), 1402 ($v_{-CH2\ bend}$), 1257 ($v_{Si-C}$). $^1$H NMR (CDCl$_3$, ppm): 0.292 (Si—CH$_3$), 7.452 (—C$_6$H$_4$). $^{13}$C{$^1$H} NMR (CDCl$_3$, ppm): 0.143 (Si—CH$_3$), 68.521 (m-C$_2$B$_{10}$H$_{10}$), 93.851 (—C≡C—), 103.381 (—C≡C—), 123.182 (p-C$_6$H$_4$), 132.393 (p-C$_6$H$_4$).

EXAMPLE 17

Synthesis of the polyarylacetylene from 1,2-dichlorotetramethyldisilane with either 3:2:1 or 5:4:1 or 10:9:1 disilane-carborane-arylacetylene ratio by the Grignard route—(Prophetic) A similar procedure as with the alternating copolymer with siloxane:carborane:arylacetylene ratio of 3:2:1 as described in Example 4 is used for the synthesis of the alternating copolymer with a 3:2:1 or 5:4:1 or 10:9:1 ratio, except that 1,2-dichlorotetramethyldisilane is used in place of the siloxane and the stoichiometric ratios of 1,2-dichlorotetramethyldisilane:arylacetylene and carborane:arylacetylene are 3:1 and 2:1 or 5:1 and 4:1 or 10:1 and 9:1, respectively.

EXAMPLE 18

Synthesis of the polyarylacetylene containing 1,2-dichlorotetraphenyldisilane by the Grignard route—1,2-Dichlorotetraphenyldisilane (Tacke, et al., Z. Naturforsch. 2002, 57b, 731-735) used in the synthesis was prepared as follows. Acetyl chloride (1.60 g, 20.4 mmol) was added to a stirred solution of 1,2-bis(diethylamino)-1,1,2,2-tetraphenyldisilane (5.00 g, 9.83 mmol) (Ref.: Tamao et al., J. Organomet. Chem. 1994, 473, 29-35) in dichloromethane (40 mL) at 0° C. and the mixture then stirred overnight at RT. The solvent was removed under reduced pressure and the resulting solid was recrystallized from toluene/petroleum ether (40-60° C.) [1:1 (v/v)] to give 3.81 g (8.75 mmol) of a colorless crystalline product (yield 89%). M. P. 106-109° C. $^1$H NMR: δ=7.26-7.69 (m, 20H, SiPh). $^{13}$C{$^1$H} NMR: δ=128.2 (C-2/C-6 or C-3/C-5, SiPh), 130.8 (C-4, SiPh), 132.2 (C-1, SiPh), 135.0 (C-2/C-6 or C-3/C-5, SiPh).

Flask # 1: A flame-dried 100 mL Schlenk flask under argon was charged with 10 mL of 1.0 M solution of ethylmagnesium bromide solution in THF (F.W.=133.27, 10 mmol). 1,4-Diethynylbenzene (0.66 mL, 5 mmol, F.W.=126.15, d=0.949) was added to the solution dropwise over a period of 40 minutes. The solution was heated to 80° C. and the heating was continued for 1.5 h resulting in the formation of a green-grey precipitate/suspension. The suspension became white in appearance when the solution was heated at 90° C. for an additional 45 min. The solution was then cooled to RT.

Flask #2: In a 100-mL flame-dried Schlenk flask under argon, m-carborane (0.72 g, 5 mmol) was dissolved in 5 mL of THF and was placed in an ice bath. n-Butyllithium in hexanes (2.5 M, 4 mL, 10 mmol) was added dropwise to the solution. The mixture was warmed to room temperature and the volatiles were then removed under vacuum. The residue was dissolved in 2 mL of THF and the mixture was cooled to 0° C. To this solution, 1,2-dichlorotetraphenyldisilane (M.W.=435.50 g/mol, 4.355 g, 10 mmol) was added slowly in batches. The resulting mixture was stirred for 3 h at room temperature.

Chain extension: The contents of flask #1 were cannulated into flask #2 and the mixture was stirred for 16 h. The mixture was then poured into 50 mL of a cold, saturated NH$_4$Cl solution and extracted three times with 75 mL each of Et$_2$O. The Et$_2$O extracts were combined, washed with 100 mL of brine, dried over anhydrous Na$_2$SO$_4$, filtered through a 1-in. pad of Celite, and the solvent was removed under vacuum. A pale orange viscous oil was obtained (98% yield).

Spectroscopic characterizations: IR (NaCl disk, cm$^{-1}$): 2156 ($v_{C\equiv C}$), 1261 ($v_{Si-C}$). $^1$H NMR (CDCl$_3$, ppm): 7.22-7.62 (m, 20H, SiPh), 7.458 (—C$_6$H$_4$). $^{13}$C{$^1$H} NMR (CDCl$_3$, ppm): 68.521 (m-C$_2$B$_{10}$H$_{10}$), 93.823 (—C≡C—), 103.345 (—C≡C—), 123.122 (p-C$_6$H$_4$), 132.345 (p-C$_6$H$_4$), 128.112-134.426 (5C, Si-Ph).

EXAMPLE 19

Synthesis of the polyarylacetylene from 1,2-dichlorotetraphenyldisilane with either 3:2:1 or 5:4:1 or 10:9:1 disilane-carborane-arylacetylene ratio by the Grignard route—(Prophetic) A similar procedure as with the alternating copolymer with siloxane:carborane:arylacetylene ratio of 3:2:1 as described in Example 4 is used for the synthesis of the alternating copolymer with a 3:2:1 or 5:4:1 or 10:9:1 ratio, except that 1,2-dichlorotetraphenyldisilane is used in place of the siloxane and the stoichiometric ratios of 1,2-dichlorotetraphenyldisilane:arylacetylene and carborane:arylacetylene are 3:1 and 2:1 or 5:1 and 4:1 or 10:1 and 9:1, respectively.

EXAMPLE 20

Synthesis of the polyarylacetylene containing 1,2-dichlorodisilane by the Grignard route—Flask # 1: A flame-dried 100 mL Schlenk flask under argon was charged with 10 mL of 1.0 M solution of ethylmagnesium bromide solution in THF (F.W.=133.27, 10 mmol). 1,4-Diethynylbenzene (0.66 mL, 5 mmol, F.W.=126.15, d=0.949) was added to the solution dropwise over a period of 40 minutes. The solution was heated to 80° C. and the heating was continued for 1.5 h resulting in the formation of a green-grey precipitate/suspension. The suspension became white in appearance when the solution was heated at 90° C. for an additional 45 min. The solution was then cooled to RT.

Flask #2: In a 100-mL flame-dried Schlenk flask under argon, m-carborane (0.72 g, 5 mmol) was dissolved in 5 mL of THF and was placed in an ice bath. n-Butyllithium in hexanes (2.5 M, 4 mL, 10 mmol) was added dropwise to the solution. The mixture was warmed to room temperature and the volatiles were then removed under vacuum. The residue was dissolved in 2 mL of THF and the mixture was cooled to 0° C. To this solution, 1,2-dichlorodisilane (M.W.=187.292 g/mol, 1.873 g, 10 mmol) was added dropwise via a gastight syringe. The resulting mixture was stirred for 3 h at room temperature.

Chain extension: The contents of flask #1 were cannulated into flask #2 and the mixture was stirred for 16 h. The mixture was then poured into 50 mL of a cold, saturated NH$_4$Cl solution and extracted three times with 75 mL each of Et$_2$O. The Et$_2$O extracts were combined, washed with 100 mL of brine, dried over anhydrous Na$_2$SO$_4$, filtered through a 1-in. pad of Celite, and the solvent was removed under vacuum. A pale orange viscous oil was obtained (99% yield).

Spectroscopic characterizations: IR (NaCl disk, cm$^{-1}$): 2196 ($v_{Si-H}$ stretch), 2185 ($v_{Si-H}$ stretch), 2175 ($v_{Si-H}$ stretch), 2152 ($v_{C\equiv C}$). $^1$H NMR (CDCl$_3$, ppm): 7.458 (—C$_6$H$_4$). $^{13}$C{$^1$H} NMR (CDCl$_3$, ppm): 68.492 (m-C$_2$B$_{10}$H$_{10}$), 93.811 (—C≡C—), 103.312 (—C≡C—), 123.058 (p-C$_6$H$_4$), 132.312 (p-C$_6$H$_4$).

EXAMPLE 21

Synthesis of the polyarylacetylene containing dimethyldichlorosilane by the Grignard route—Flask # 1: A flame-dried 100 mL Schlenk flask under argon was charged with 20 mL of 1.0 M solution of ethylmagnesium bromide solution in THF (F.W.=133.27, 20 mmol). 1,4-Diethynylbenzene (1.32 mL, 10 mmol, F.W.=126.15, d=0.949) was added to the solution dropwise over a period of 40 minutes. The solution was heated to 80° C. and the heating was continued for 1.5 h resulting in the formation of a green-grey precipitate/suspension. The suspension became white in appearance when the solution was heated at 90° C. for an additional 45 min. The solution was then cooled to RT.

Flask #2: In a 100-mL flame-dried Schlenk flask under argon, m-carborane (1.44 g, 10 mmol) was dissolved in 5 mL of THF and was placed in an ice bath. n-Butyllithium in hexanes (2.5 M, 8 mL, 20 mmol) was added dropwise to the solution. The mixture was warmed to room temperature and the volatiles were then removed under vacuum. The residue was dissolved in 2 mL of THF and the mixture was cooled to 0° C. To this solution, dimethyldichlorosilane (M.W.=129.06 g/mol, 2.43 mL, 2.58 g, 20 mmol) was added dropwise via a gastight syringe. The resulting mixture was stirred for 3 h at room temperature.

Chain extension: The contents of flask #1 were cannulated into flask #2 and the mixture was stirred for 16 h. The mixture was then poured into 50 mL of a cold, saturated NH$_4$Cl solution and extracted three times with 75 mL each of Et$_2$O. The Et$_2$O extracts were combined, washed with 100 mL of brine, dried over anhydrous Na$_2$SO$_4$, filtered through a 1-in. pad of Celite, and the solvent was removed under vacuum. A pale orange viscous oil was obtained (96% yield).

Spectroscopic characterizations: IR (NaCl disk, cm$^{-1}$): 2954 ($v_{C-H}$, Si—CH$_3$), 2152 ($v_{C\equiv C}$), 1257 ($v_{Si-C}$). $^1$H NMR (CDCl$_3$, ppm): 0.298 (Si—CH$_3$), 7.452 (—C$_6$H$_4$). $^{13}$C{$^1$H} NMR (CDCl$_3$, ppm): 0.182 (Si—CH$_3$), 68.548 (m-C$_2$B$_{10}$H$_{10}$), 93.842 (—C≡C—), 103.364 (—C≡C—), 123.193 (p-C$_6$H$_4$), 132.401 (p-C$_6$H$_4$).

EXAMPLE 22

Synthesis of the polyarylacetylene from dimethyldichlorosilane with either 3:2:1 or 5:4:1 or 10:9:1 silane-carborane-arylacetylene ratio by the Grignard route—(Prophetic) A similar procedure as with the alternating copolymer with siloxane:carborane:arylacetylene ratio of 3:2:1 as described in Example 4 is used for the synthesis of the alternating copolymer with a 3:2:1 or 5:4:1 or 10:9:1 ratio, except that dimethyldichlorosilane is used in place of the siloxane and the stoichiometric ratios of dimethyldichlorosilane:arylacetylene and carborane:arylacetylene are 3:1 and 2:1 or 5:1 and 4:1 or 10:1 and 9:1, respectively.

EXAMPLE 23

Synthesis of the polyarylacetylene containing diphenyldichlorosilane by the Grignard route—Flask # 1: A flame-dried 100 mL Schlenk flask under argon was charged with 20 mL of 1.0 M solution of ethylmagnesium bromide solution in THF (F.W.=133.27, 20 mmol). 1,4-Diethynylbenzene (1.32 mL, 10 mmol, F.W.=126.15, d=0.949) was added to the solution dropwise over a period of 40 minutes. The solution was heated to 80° C. and the heating was continued for 1.5 h resulting in the formation of a green-grey precipitate/suspension. The suspension became white in appearance when the solution was heated at 90° C. for an additional 45 min. The solution was then cooled to RT.

Flask #2: In a 100-mL flame-dried Schlenk flask under argon, m-carborane (1.44 g, 10 mmol) was dissolved in 5 mL of THF and was placed in an ice bath. n-Butyllithium in hexanes (2.5 M, 8 mL, 20 mmol) was added dropwise to the solution. The mixture was warmed to room temperature and the volatiles were then removed under vacuum. The residue was dissolved in 2 mL of THF and the mixture was cooled to 0° C. To this solution, diphenyldichlorosilane (M.W.=253.20 g/mol, 4.15 mL, 5.064 g, 20 mmol) was added dropwise via a gastight syringe. The resulting mixture was stirred for 3 h at room temperature.

Chain extension: The contents of flask #1 were cannulated into flask #2 and the mixture was stirred for 16 h. The mixture was then poured into 50 mL of a cold, saturated NH$_4$Cl solution and extracted three times with 75 mL each of Et$_2$O. The Et$_2$O extracts were combined, washed with 100 mL of brine, dried over anhydrous Na$_2$SO$_4$, filtered through a 1-in. pad of Celite, and the solvent was removed under vacuum. A pale orange viscous oil was obtained (97% yield).

Spectroscopic characterizations: IR (NaCl disk, cm$^{-1}$): 2152 ($v_{C\equiv C}$), 1257 ($v_{Si-C}$). $^1$H NMR (CDCl$_3$, ppm): 0.292 (Si—CH$_3$), 7.22-7.62 (m, 20H, SiPh), 7.458 (—C$_6$H$_4$). $^{13}$C{$^1$H} NMR (CDCl$_3$, ppm): 0.143 (Si—CH$_3$), 68.521 (m-C$_2$B$_{10}$H$_{10}$), 93.832 (—C≡C—), 103.346 (—C≡C—), 123.122 (p-C$_6$H$_4$), 132.343 (p-C$_6$H$_4$), 128.112-134.426 (5C, Si-Ph).

EXAMPLE 24

Synthesis of the polyarylacetylene from diphenyldichlorosilane with either 3:2:1 or 5:4:1 or 10:9:1 silane-carborane-arylacetylene ratio by the Grignard route—(Prophetic) A similar procedure as with the alternating copolymer with siloxane:carborane:arylacetylene ratio of 3:2:1 as described in Example 4 is used for the synthesis of the alternating copolymer with a 3:2:1 or 5:4:1 or 10:9:1 ratio, except that diphenyldichlorosilane is used in place of the siloxane and the stoichiometric ratios of diphenyldichlorosilane:arylacetylene and carborane:arylacetylene are 3:1 and 2:1 or 5:1 and 4:1 or 10:1 and 9:1, respectively.

EXAMPLE 25

Synthesis of the polyarylacetylene containing dichlorosilane by the Grignard route—(Caution: The synthesis has to be carried out in a glove box as dichlorosilane can form pyrophoric reaction products on contact with water or amines.) Flask # 1: A dried 100 mL Schlenk flask under argon was charged with 10 mL of 1.0 M solution of ethylmagnesium bromide solution in THF (F.W.=133.27, 10 mmol) in a glove box. 1,4-Diethynylbenzene (0.66 mL, 5 mmol, F.W.=126.15, d=0.949) was added to the solution dropwise over a period of 40 minutes. The solution was heated to 80° C. and the heating was continued for 1.5 h resulting in the formation of a green-grey precipitate/suspension. The suspension became white in appearance when the solution was heated at 90° C. for an additional 45 min. The solution was then cooled to RT.

Flask #2: In a 100-mL flame-dried Schlenk flask under argon, m-carborane (0.72 g, 5 mmol) was dissolved in 5 mL of THF and was cooled to 0° C. with the refrigeration unit in a glove box. n-Butyllithium in hexanes (2.5 M, 4 mL, 10 mmol) was added dropwise to the solution. The mixture was warmed to room temperature and the volatiles were then removed under vacuum. The residue was dissolved in 2 mL of THF and the mixture was cooled to 0° C. To this solution, dichlorosilane (M.W.=101.01 g/mol, 1.01 g, 10 mmol) was added dropwise via a gastight syringe. The resulting mixture was stirred for 3 h at room temperature.

Chain extension: The contents of flask #1 were cannulated into flask #2 and the mixture was stirred for 16 h. The mixture was then poured into 50 mL of a cold, saturated NH$_4$Cl solution and extracted three times with 75 mL each of Et$_2$O. The Et$_2$O extracts were combined, washed with 100 mL of brine, dried over anhydrous Na$_2$SO$_4$, filtered through a 1-in. pad of Celite, and the solvent was removed under vacuum. A pale orange viscous oil was obtained (94% yield).

Spectroscopic characterizations: IR (NaCl disk, cm$^{-1}$): 2198 ($v_{Si-H}$ stretch), 2189 ($v_{Si-H}$ stretch), 2178 ($v_{Si-H}$ stretch), 2154 ($v_{C\equiv C}$). $^1$H NMR (CDCl$_3$, ppm): 7.459 (—C$_6$H$_4$). $^{13}$C{$^1$H} NMR (CDCl$_3$, ppm): 68.498 (m-C$_2$B$_{10}$H$_{10}$), 93.819 (—C≡C—), 103.322 (—C≡C—), 123.063 (p-C$_6$H$_4$), 132.322 (p-C$_6$H$_4$).

EXAMPLE 26

Synthesis of the polyarylacetylene containing various siloxane units from the disodium derivative of the 1,4-diethynylbenzene—A flame-dried 250 mL Schlenk flask under argon was charged with 50 mL of dry ether under dry argon. Sodium metal (0.92 g, 40 mmol) was added to the flask which was followed by a gradual addition of 1,4-diethynylbenzene (2.52 g, 20 mmol). The mixture was stirred for 48 h at room temperature. The evolved $H_2$ gas was released frequently through the vacuum line by reducing or stopping the flow of argon. The dark grey precipitate was filtered, washed with ether, dried, and collected under argon. The precipitate was taken as a dispersion in 50 mL of dry THF and 1,3-dichlorotetramethyldisiloxane, 1,5-dichlorohexamethyltrisiloxane, 1,7-dichlorooctamethyltetrasiloxane, or 1,9-dichlorodecamethylpentasiloxane (20 mmol) was added in 40 min. The solution was refluxed overnight resulting in the production of a pale orange solution. The mixture was cooled to RT. To this mixture, 0.3 mL of the corresponding dichlorosiloxane was further added dropwise and the mixture was further refluxed overnight. The mixture was transferred to a cold aqueous $NH_4Cl$ solution resulting in a yellow solution and dissolution of NaCl. The pH of the mixture was adjusted to 7 using 1 M HCl. The product was extracted by washing with several batches of diethyl ether in a separatory funnel. Subsequently, the ether extracts were dried over $MgSO_4$, filtered through a pad of Celite and concentrated in vacuo. A pale yellow/orange product was obtained in 98% yield.

Spectroscopic characterizations: The product from 1,3-dichlorotetramethyldisiloxane: IR (NaCl disk, $cm^{-1}$): 3065 ($v_{C-H}$, $C_6H_5$), 2959 ($v_{C-H}$, Si—$CH_3$), 2155 ($v_{C\equiv C}$), 1259 ($v_{Si-C}$), 1074 ($v_{Si-O}$). $^1H$ NMR ($CDCl_3$, ppm): 0.381 (Si—$CH_3$), 7.431 (—$C_6H_4$). $^{13}C\{^1H\}$ NMR ($CDCl_3$, ppm): 2.283 (Si—$CH_3$), 94.849 (—C≡C—), 103.842 (—C≡C—), 123.141 (p-$C_6H_4$), 132.378 (p-$C_6H_4$).

The product from 1,5-dichlorohexamethyltrisiloxane: IR (NaCl disk, $cm^{-1}$): 3065 ($v_{C-H}$, $C_6H_5$), 2962 ($v_{C-H}$, Si—$CH_3$), 2156 ($v_{C\equiv C}$), 1260 ($v_{Si-C}$), 1076 ($v_{Si-O}$). $^1H$ NMR ($CDCl_3$, ppm): 0.17-0.38 (Si—$CH_3$), 7.437 (—$C_6H_4$). $^{13}C\{^1H\}$ NMR ($CDCl_3$, ppm): 1.728 (Si—$CH_3$), 2.283 (Si—$CH_3$), 94.849 (—C≡C—), 103.842 (—C≡C—), 123.152 (p-$C_6H_4$), 132.397 (p-$C_6H_4$).

The product from 1,7-dichlorooctamethyltetrasiloxane: IR (NaCl disk, $cm^{-1}$): 3065 ($v_{C-H}$, $C_6H_5$), 2962 ($v_{C-H}$, Si—$CH_3$), 2156 ($v_{C\equiv C}$), 1260 ($v_{Si-C}$), 1076 ($v_{Si-O}$). $^1H$ NMR ($CDCl_3$, ppm): 0.10-0.36 (Si—$CH_3$), 7.437 (—$C_6H_4$). $^{13}C\{^1H\}$ NMR ($CDCl_3$, ppm): 1.728 (Si—$CH_3$), 2.283 (Si—$CH_3$), 94.849 (—C≡C—), 103.842 (—C≡C—), 123.175 (p-$C_6H_4$), 132.402 (p-$C_6H_4$).

The product from 1,9-dichlorodecamethylpentasiloxane: IR (NaCl disk, $cm^{-1}$): 3068 ($v_{C-H}$, $C_6H_5$), 2967 ($v_{C-H}$, Si—$CH_3$), 2156 ($v_{C\equiv C}$), 1260 ($v_{Si-C}$), 1076 ($v_{Si-O}$). $^1H$ NMR ($CDCl_3$, ppm): 0.09-0.38 (Si—$CH_3$), 7.432 (—$C_6H_4$). $^{13}C\{^1H\}$ NMR ($CDCl_3$, ppm): 0.08-0.37 (Si—$CH_3$), 94.892 (—C≡C—), 103.8785 (—C≡C—), 123.102 (p-$C_6H_4$), 132.375 (p-$C_6H_4$).

EXAMPLE 27

Synthesis of the polyarylacetylene containing various siloxane units by Pd-catalyzed Sonagashira coupling reaction involving 1,4-diethynylbenzene—To initiate the Pd-catalyzed Sonagashira coupling reaction, the respective dichlorosiloxane, viz. 1,3-dichlorotetramethyldisiloxane, 1,5 dichlorohexamethyltrisiloxane, 1,7-dichlorooctamethyltetrasiloxane, or 1,9-dichlorodecamethylpentasiloxane was initially converted to their diethynyl variant by reaction with ethynylmagnesium bromide.

Production of the polyarylacetylene from the diethynyl compound of the respective dichlorosiloxane: In a 250 mL Schlenk flask, a mixture of the respective diethynylsiloxane (20 mmol), 1,4-diiodobenzene (6.46 g, 20 mmol), $(PPh_3)_2PdCl_2$ (0.02 g, 0.028 mmol), CuI (0.086 g, 0.450 mmol) and $PPh_3$ (0.20 g, 0.762 mmol) in triethylamine (60 mL) and toluene (60 mL) was degassed and stirred under $N_2$ at 90° C. for 16 h. After 24 hours of reaction, the mixture was allowed to cool to 50° C., and a few drops of the respective diethynyl siloxane was added, and the mixture was stirred for a further 1 h. The product was extracted by washing with several batches of diethyl ether in a reparatory funnel. Subsequently, the ether extracts were dried over $MgSO_4$, filtered through a pad of Celite and concentrated in vacuo. A pale yellow/orange product was obtained in 98% yield.

Spectroscopic characterizations: The spectral characteristics of the polyarylacetylenes obtained from 1,3-dichlorotetramethyldisiloxane, 1,5-dichlorohexamethyltrisiloxane, 1,7-dichlorooctamethyltetrasiloxane, or 1,9-dichlorodecamethylpentasiloxane were similar to such products obtained from the disodium derivative reactions.

EXAMPLE 28

Synthesis of the polyarylacetylene containing various siloxane units by the Grignard route involving 1,4-diethynylbenzene—A flame-dried 250 mL Schlenk flask under argon was charged with 40 mL of 1.0 M solution of ethylmagnesium bromide solution in THF (F.W.=133.27, 40 mmol). 2.64 mL of 1,4-diethynylbenzene (20 mmol, F.W.=126.15, d=0.949) was added to the solution dropwise over a period of 40 minutes. The solution was heated to 80° C. and the heating was continued for 1.5 h resulting in the formation of a green-grey precipitate/suspension. The suspension became white in appearance when the solution was heated at 90° C. for an additional 45 min. The solution was then cooled to RT and the respective dichlorosiloxane, viz. 1,3-dichlorotetramethyldisiloxane, 1,5-dichlorohexamethyltrisiloxane, 1,7-dichlorooctamethyltetrasiloxane, or 1,9-dichlorodecamethylpentasiloxane (20 mmol) was added in 40 min. 5 mL of THF was also added to the mixture at this point. The solution was refluxed for an hour when the dissolution of the white precipitate and the production of a pale orange solution resulted. The mixture was stirred overnight at RT. To this mixture, 0.3 mL of the respective dichlorosiloxane was further added dropwise and the mixture was stirred at RT for an hour. The mixture was transferred to a cold aqueous $NH_4Cl$ solution resulting in a yellow solution and copious amount of a white precipitate (MgBrCl). The pH of the mixture was adjusted to 7 using 1 M HCl. The product was extracted by washing with several batches of diethyl ether in a separatory funnel. Subsequently, the ether extracts were dried over $MgSO_4$, filtered through a pad of Celite and concentrated in vacuo. A pale yellow/orange product was obtained in 98% yield.

Spectroscopic characterizations: The spectral characteristics of the polyarylacetylenes obtained from 1,3-dichlorotetramethyldisiloxane, 1,5 dichlorohexamethyl trisiloxane, 1,7-dichlorooctamethyltetrasiloxane, or 1,9-dichlorodecamethylpentasiloxane were similar to such products obtained from the disodium derivative reactions.

Obviously, many modifications and variations are possible in light of the above teachings. It is therefore to be understood that the claimed subject matter may be practiced otherwise than as specifically described. Any reference to claim elements in the singular, e.g., using the articles "a," "an," "the," or "said" is not construed as limiting the element to the singular.

What is claimed is:

1. A compound comprising the repeat unit:

wherein each R is an independently selected organic group;
wherein Cb is a carborane group;
wherein —$C_6H_4$— is phenylene;
wherein each m is a nonnegative integer;
wherein q is 0 or 1, with the proviso that if q is 0 then m is 0 or 1; and
wherein p is a positive integer.

2. The compound of claim 1, wherein each R is independently selected from hydrogen, methyl, and phenyl.

3. The compound of claim 1, wherein Cb is m-carborane.

4. The compound of claim 1;
wherein the repeat unit is:

wherein each R is independently selected from methyl and phenyl;
wherein m is an integer from 1 to 5; and
wherein p is an integer from 1 to 9.

5. The compound of claim 1;
wherein the repeat unit is:

wherein each R is independently selected from hydrogen, methyl, and phenyl; and
wherein p is an integer from 1 to 9.

6. The compound of claim 1;
wherein the repeat unit is:

wherein each R is independently selected from hydrogen, methyl, and phenyl; and
wherein p is an integer from 1 to 9.

7. The compound of claim 1;
wherein the compound is:

and
wherein M is H, Li, Na, K, or MgX', wherein X' is a halogen.

8. A crosslinked polymer made by curing the ethynyl groups of the compound of claim 1.

9. The crosslinked polymer of claim 8, wherein the curing is by hydrosilylation, Diels-Alder reaction, or thermal polymerization through the ethynyl groups.

10. A method comprising:
providing an acetylene-containing compound having the formula:

wherein —$C_6H_4$— is phenylene; and
wherein M is Li, Na, K, or MgX', wherein X' is a halogen; and
reacting the acetylene-containing compound with a carborane-containing compound having the formula:

wherein each R is an independently selected organic group;
wherein Cb is a carborane group;
wherein X is a halogen;
wherein each m is a nonnegative integer;
wherein q is 0 or 1, with the proviso that if q is 0 then m is 0 or 1; and
wherein p is a positive integer; and
wherein the product of the reaction is a compound comprising the repeat unit:

11. The method of claim 10, wherein the acetylene-containing compound and the carborane-containing compound are reacted in an equimolar ratio.

12. The method of claim 10, wherein the acetylene-containing compound and the carborane-containing compound are reacted in a 2:1 molar ratio.

13. The method of claim 10, further comprising:
curing the ethynyl groups of the compound to make a crosslinked polymer.

14. A method comprising:
providing an acetylene-siloxane-carborane compound having the formula:

wherein each R is an independently selected organic group;
wherein Cb is a carborane group;
wherein each m is a nonnegative integer;
wherein q is 0 or 1, with the proviso that if q is 0 then m is 0 or 1; and
wherein p is a positive integer; and
reacting the acetylene-siloxane-carborane compound with a phenyl-containing compound having the formula under metal-catalyzed coupling conditions:

wherein —$C_6H_4$— is phenylene;
wherein X is a halogen; and
wherein the product of the reaction is a compound comprising the repeat unit:

15. The method of claim 14, wherein the acetylene-containing compound and the carborane-containing compound are reacted in an equimolar ratio.

16. The method of claim 14, further comprising:
curing the ethynyl groups of the compound to make a crosslinked polymer.

* * * * *